(12) United States Patent
Schofield et al.

(10) Patent No.: US 7,662,854 B2
(45) Date of Patent: Feb. 16, 2010

(54) HIF HYDROXYLASE INHIBITORS

(75) Inventors: Christopher Joseph Schofield, Oxford (GB); Patrick Henry Maxwell, London (GB); Christopher William Pugh, Oxford (GB); Peter John Ratcliffe, Oxford (GB)

(73) Assignee: ISIS Innovation Limited (GB)

( * ) Notice: Subject to any disclaimer, the term of this patent is extended or adjusted under 35 U.S.C. 154(b) by 0 days.

(21) Appl. No.: 11/518,157

(22) Filed: Sep. 11, 2006

(65) Prior Publication Data

US 2007/0066576 A1 Mar. 22, 2007

Related U.S. Application Data

(63) Continuation of application No. 10/508,423, filed as application No. PCT/GB03/01239 on Mar. 21, 2003, now abandoned.

(30) Foreign Application Priority Data

Mar. 21, 2002 (GB) ................... 0206711.4

(51) Int. Cl.
*A61K 31/194* (2006.01)
*A61K 31/225* (2006.01)
*A61K 31/164* (2006.01)

(52) U.S. Cl. .................. 514/557; 514/561; 514/645

(58) Field of Classification Search .......... 514/613, 514/619, 617, 557, 561, 645; 564/151, 163, 564/164, 169
See application file for complete search history.

(56) References Cited

U.S. PATENT DOCUMENTS

| | | | |
|---|---|---|---|
| 4,273,779 A | 6/1981 | Finch | |
| 4,446,038 A | 5/1984 | Schlicht et al. | |
| 4,623,733 A | 11/1986 | Higashide et al. | |
| 4,752,602 A | 6/1988 | Lipsky et al. | |
| 4,797,471 A | 1/1989 | Teetz et al. | |
| 5,206,343 A | 4/1993 | Henke et al. | |
| 5,439,930 A | 8/1995 | Seredenin et al. | |
| 6,200,974 B1 | 3/2001 | Edwards et al. | |

FOREIGN PATENT DOCUMENTS

| | | |
|---|---|---|
| DE | 1 620 359 | 12/1969 |
| DE | 44 10 453 A1 | 9/1995 |
| EP | 0 148 752 A2 | 7/1985 |
| EP | 0 178 665 | 4/1986 |
| EP | 0 293 029 A1 | 11/1988 |
| EP | 0 185 225 B1 | 1/1990 |
| FR | 6.969 M | 6/1969 |
| FR | 2 662 359 | 11/1991 |
| GB | 1226394 | 3/1971 |
| JP | 61218522 | 9/1986 |
| JP | 61249993 | 11/1986 |
| JP | 7138167 | 5/1995 |
| RU | 2001588 | 10/1993 |
| RU | 2079307 | 5/1997 |
| RU | 2 111 746 | 5/1998 |
| RU | 2 141 943 | 11/1999 |
| WO | WO 97/24145 | 7/1997 |
| WO | WO 99/07729 | 2/1999 |
| WO | WO 00/71514 A1 | 11/2000 |
| WO | WO 00/74725 A1 | 12/2000 |
| WO | WO 01/93841 A2 | 12/2001 |
| WO | WO 02/074981 A2 | 9/2002 |

OTHER PUBLICATIONS

Cited ref-STN-11518157M.*
Communication from European Patent Office issued in Application No. 03712396.5-1521, dated May 22, 2007 (5 pages).

(Continued)

*Primary Examiner*—Kamal A Saeed
*Assistant Examiner*—Yong Chu
(74) *Attorney, Agent, or Firm*—Finnegan, Henderson, Farabow, Garrett & Dunner LLP

(57) ABSTRACT

The invention provides a compound of one of the formulae (A), (B), (C), (D), (E), (F) as herein defined, or a salt thereof, for use in the treatment of a condition associated with increased or decreased HIF levels or activity, or a condition in which an increase or decrease in HIF levels or activity may be beneficial.

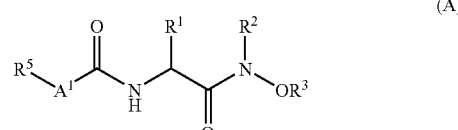

(A)

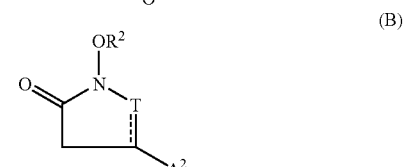

(B)

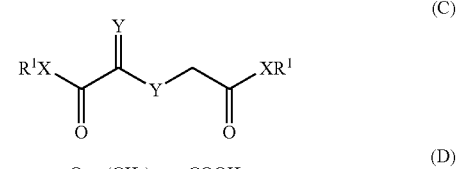

(C)

Q—(CH$_2$)$_m$—COOH (D)

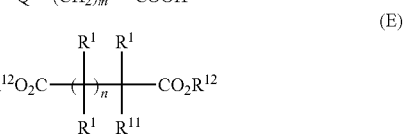

(E)

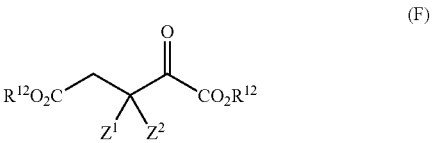

(F)

3 Claims, 5 Drawing Sheets

OTHER PUBLICATIONS

Isao; "Oligopeptide;" Patent Abstracts of Japan; Publication No. 58099453, publication date Jun. 13, 1983.

Thouin et al.; "Effective Synthesis of Enantiopure Hydroxamates by Displacement of Resin-Bound Esters with Hydroxylamine;" Tetrahedron Letters 41; pp. 457-460; 2000.

Walter et al.; "Hydroxamate Inhibitors of Aeromonas Hydrophila AE036 Metallo-β-Lactamase;" Bioorganic Chemistry; vol. 27; pp. 35-40; 1999.

Clifton et al.; "Structure of Proline 3-hydroxylase. Evolution of the Family of 2-oxoglutarate Dependent Oxygenases;" Eur. J. Biochem.; vol. 268; pp. 6625-6636; 2001.

Walter et al.; "Synthesis of Metallo-β-Lactamase Inhibitors;" Tetrahedron; vol. 53, No. 21; pp. 7275-7290; 1997.

Jaakkola et al.; Targeting of HIF-α to the von Hippel-Lindau Ubiquitylation Complex by $O_2$-Regulated Prolyl Hydroxylation; Science; vol. 292; Apr. 20, 2001.

Blodgett et al.; "Specific Cleavage of Peptides Containing an Aspartic Acid (β-Hydroxamic Acid) Residue;" Journal of the American Chemical Society; vol. 107, No. 14, pp. 4305-4313; 1985.

Bender et al.; "Sigmoid and Bell-Shaped pH-Rate Profiles in α-Chymotryspin-Catalyzed Hydrolyses. A Mechanistic Correlation;" Journal of the American Chemical Society; vol. 85; pp. 358-359; 1963.

Zukowski et al.; "Modification of 6-Aminopenicillanic Acid Derivatives;" Chemical Abstracts, ol. 86; No. 11; p. 603; 1977.

Database Crossfire Beilstein XP002244406; Registration No. 5623186; 1993.

Database Crossfire Beilstein XP002244407; Registration No. 2900977; 1998.

Database Crossfire Beilstein XP002244408; Registration No. 4152395; 1995.

Kwon et al.; "Photooxygenation of Ascorbic Acid Derivatives and Model Compounds;" Journal of the American Chemical Society; vol. 111, No. 5, pp. 1854-1860; 1989.

Wehbie et al.; "Rat Liver γ-Butyrobetaine Hydroxylase Catalyzed Reaction: Influence of Potassium, Substrates, and Substrate Analogues on Hydroxylation and Decarboxylation;" Biochemistry; vol. 27; pp. 2222-2228; 1988.

Balsiger et al.; "Synthesis of Potential Anticancer Agents. XVIII. Analogs of Carbamoyl Phosphate;" Chemical Abstracts; vol. 54, No. 11; p. 10855; 1960.

Takayama et al.; "Selective Inhibition of β-1,4- and α-1,3-Galactosyltransferases: Donor Sugar-Nucleotide Based Approach;" Bioorganic & Medicinal Chemistry; vol. 7; pp. 401-409; 1999.

Cunliffe et al.; "Novel Inhibitors of Prolyl 4-Hydroxylase. 3. Inhibition by the Substrate Analogue N-Oxaloglycine and Its Derivatives;" Journal of Medicinal Chemistry; vol. 35; pp. 2652-2658; 1992.

Hoffmann et al.; "A Peptide Synthesis via Hydroxamic Acids;" Journal of Organic Chemistry; vol. 29; pp. 748-751; 1964.

Freedman et al.; "Structural Basis for Recruitment of CBP/p300 by Hypoxia-Inducible Factor-1α;" PNAS; vol. 99, No. 8; pp. 5367-5372; Apr. 16, 2002.

Lando et al.; "Asparagine Hydroxylation of the HIF Transactivation Domain: A Hypoxic Switch;" Science; vol. 295; pp. 858-861; Feb. 1, 2002.

Lando et al.; "FIH-1 is an Asparaginyl Hydroxylase Enzyme that Regulates the Transcriptional Activity of Hypoxia-Inducible Factor;" Genes & Development; vol. 16; pp. 1466-1471; 2002.

Lee et al.; "The Structure-Activity Relationships of the Triketone Class of HPPD Herbicides;" Pesticide Science; vol. 54; pp. 377-384; 1998.

U.K. Patent Office Search Report for Application No. GB 0206711.4.

Otani et al., "N-Benzoyl derivatives of amino acids and amino acid analogs as growth inhibitors in microbial antitumor screen," J. Pharm. Sci., vol. 68, pp. 1366-1369, Nov. 1979.

International Search Report for Application No. PCT/GB03/01239.

The Merck Index, "Tricarballylic Acid", $12^{th}$ Edition, Item 9752, (1996), p. 1641.

Patent Abstract of Japan vol. 007, No. 201 (C-184), & JP 58 099453 A, 1983.

Chem-Impex International, Inc. company on-line catalog product listing, 2009.

Zukowski, Edward, et al., "Modification of 6-aminopenicillanic Acid Derivatives", Chemical Abstracts, vol. 86, No. 11, Mar. 14, 1977, p. 603, Abstract No. 72508v.

Balsiger, Rudolf W., et al., "Synthesis of Potential Anticancer Agents", Chemical Abstracts, vol. 54, No. 11, Jun. 10, 1960, p. 10855, Abstract No. 10856d.

* cited by examiner

HIF HYDROXYLASE INHIBITORS

This application is a continuation of U.S. patent application Ser. No. 10/508,423, filed Nov. 10, 2004, now abandoned which is a national stage application of International Application No. PCT/GB03/012939, filed Mar. 21, 2003, which claims benefit of priority to GB 0206711.4, filed Mar. 21, 2002, the disclosures of which are incorporated by reference.

FIELD OF INVENTION

The present invention relates to compounds which modulate 2OG (2-oxoglutarate) dependent oxygenases, in particular prolyl hydroxylases. These may be useful as modulators of HIF (hypoxia inducible factor) alpha (HIF-α) prolyl hydroxylase.

BACKGROUND OF INVENTION

The transcription factor HIF (hypoxia inducible factor) system is a key regulator of responses to hypoxia, occupying a central position in oxygen homeostasis in a wide range of organisms. A large number of transcriptional targets have been identified, with critical roles in angiogenesis, erythropoiesis, energy metabolism, inflammation, vasomotor function, and apoptotic/proliferative responses. The system is essential for normal development, and plays a key role in pathophysiological responses to ischaemia/hypoxia. HIF is also important in cancer, in which it is commonly upregulated, and has major effects on tumour growth and angiogenesis. The HIF DNA binding complex consists of a heterodimer of α and β subunits. Regulation by oxygen occurs through hydroxylation of the α-subunits, which are rapidly destroyed by the proteasome in oxygenated cells. This involves binding of HIF-α-subunits by the von Hippel-Lindau tumour suppressor protein (pVHL), with pVHL acting as the, or part of the, recognition component for a ubiquitin ligase that promotes ubiquitin dependent proteolysis through interaction with a specific sequence or sequences in HIF-α-subunits. In hypoxia, this process is suppressed, so stabilizing HIF-α and permitting transcriptional activation via the HIF α, β.

DISCLOSURE OF THE INVENTION

Figure 1:
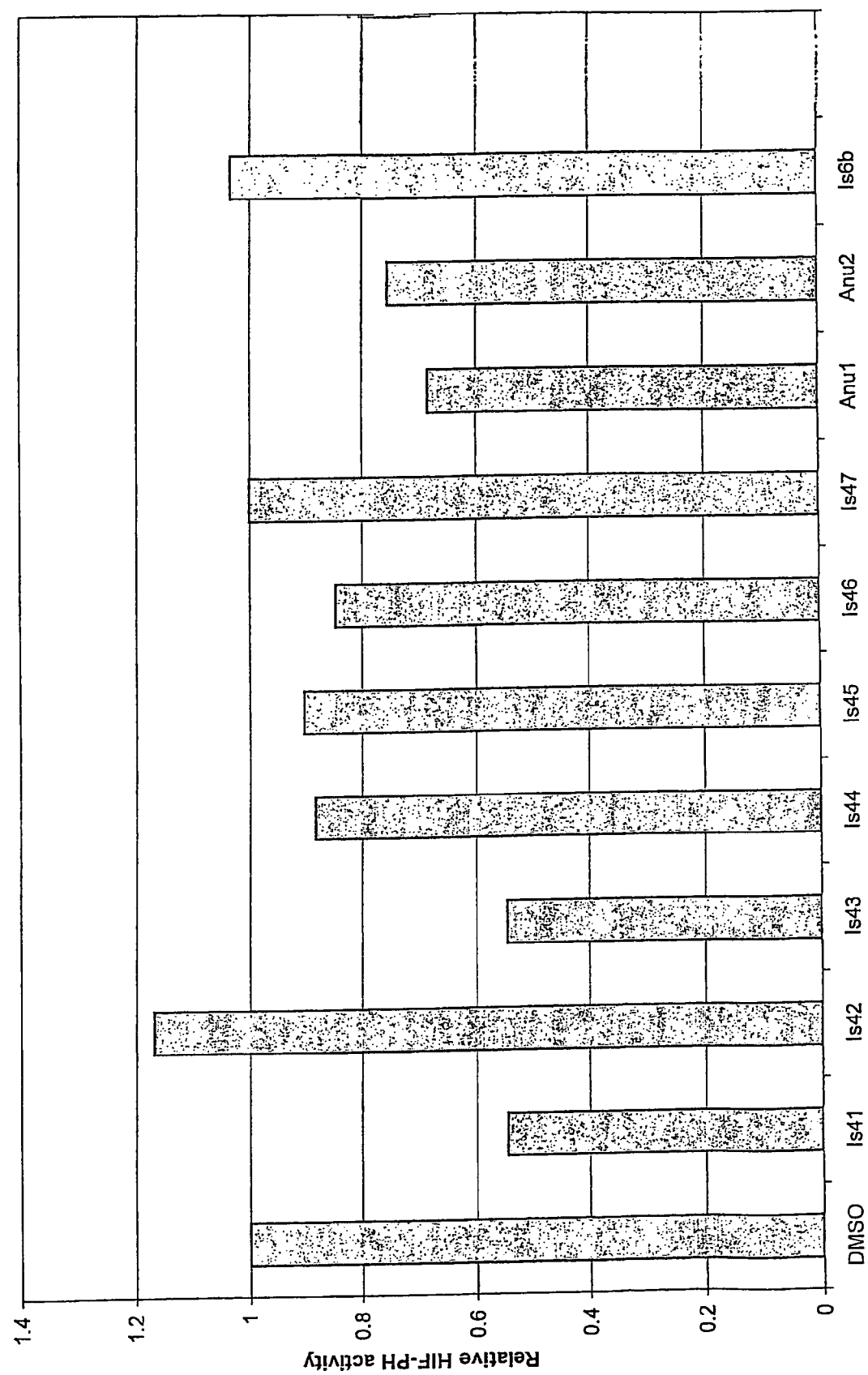
FIGS. 1 to 5 show HIF hydroxylase activity in the presence of a particular inhibitor relative to that seen in the absence of the inhibitor (the DMSO/Tris control).

In our British Application No. 0118952.1 we disclose a polypeptide comprising:
(a) the amino acid sequence of SEQ ID NO: 2, 4 or 6 having HIF hydroxylase activity;
(b) a variant thereof having at least 60% identity to the amino acid sequence of SEQ ID NO: 2, 4 or 6 and having hydroxylase activity; or
(c) a fragment of either thereof having HIF-α hydroxylase activity.
Preferably, the polypeptides have prolyl hydroxylase activity and require Fe(II) for activity.
They are related by sequence to non-haem oxygenases for which crystal structures are known, e.g. proline-3-hydroxylase (Clifton et al, Eur. J. Biochem, 2001, 268, 6625-6636).
It also discloses polynucleotides which encode the polypeptides as well as expression vectors comprising the polynucleotide and antibodies capable of specifically binding the polypeptide. We also disclose assays for identifying modulators of the activity of the HIF hydroxylase as well as the use of modulators such as inhibitors of the activity of the peptides in the treatment of a condition or disease associated with altered HIF levels with respect to healthy (or normal) levels, and the treatment of conditions where an alteration in the HIF levels or activity would be beneficial.

Inhibitors of the 2-OG dependent enzyme collagen prolyl-4-hydroxylase (CPH) are well known in the art and have been previously proposed for use in the treatment of lung fibrosis, skin fibrosis (scleroderma), atherosclerosis and other conditions associated with collagen biosynthesis. Inhibitors of para-hydroxyphenylpyruvate oxygenase (a non-haem oxygenase employing ferrous iron as a co-factor) such as triketones are used as herbicides (Lee D. et al (1998) Pestic. Sci. 54(4) 377-384). We have disclosed that certain of these CPH inhibitors (and other components) also inhibit the biological (i.e. HPH) activity of an PHD polypeptide. A CPH inhibitor or modified CPH inhibitor which inhibits the biological activity of an PHD polypeptide may be used in the treatment of a condition associated with reduced or suboptimal HIF levels or activity, or a condition in which an increase in HIF levels or activity may be beneficial, for example ischaemia, wound healing, auto-, allo-, and xeno-transplantation, systemic high blood pressure, cancer, inflammatory disorders, and metabolic disorders.

Various methods and uses of modulators which inhibit, potentiate, increase or stimulate hydroxylation of HIF-α by an PHD polypeptide are disclosed. The purpose of disruption, interference with or modulation of the hydroxylation of HIF-1α by a PHD polypeptide may be to modulate cellular functions such as angiogenesis, erythropoiesis, energy metabolism, inflammation, matrix metabolism, vasomotor function, and apoptotic/proliferative responses and pathophysiological responses to ischaemia/hypoxia, all of which are mediated by HIFα as discussed above.

Compounds which modulate 2OG oxygenases, in particular CPH may be useful as modulators of HIF prolyl hydroxylase, or may be used as 'lead' compounds which may be modified and/or optimised to develop modulators of HIF prolyl hydroxylase, in particular selective modulators are described.

Some of these compounds generally possess the formula:

$$R^1A^*B^*C^*D^*(R^2)_y \qquad (A)$$

where the group $R^1$ is capable of forming an electrostatic interaction with the sidechain of the arginine residue which, together with other residues, binds the 5-carboxylate of 2-oxoglutarate during catalysis, A*B is a chain of two atoms which are, independently, carbon, oxygen, nitrogen or sulphur, which chain can be functionalised, y is 0 or 1 and C*D is a chain of two atoms which are, independently, carbon, oxygen, nitrogen, or sulphur, which chain can be functionalised, A, B, C and D being linked to one another by a single and/or double and/or triple bond such that when y is 0 or 1 at least one of the atoms of which is capable of chelating with a, metal group and when y is 1 said chain is attached to $R^2$ which is capable of chelating with a metal group. Generally at least one of A, B, C and D is not carbon. Typical chains include C—N—C—C and C—O—C—C and C—C—C=O. The chain atoms can form part of a ring.

New classes of modulators of HIF prolyl hydroxylase have been found, according to the present invention. These possess the following formulae (A) to (F)

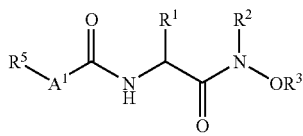
(A)

where each of $R^1$ and $R^5$ is independently H, OH, SH, a branched or straight $C_1$ to $C_6$ alkyl chain optionally containing 1 or more eg. 2 N, S, O or P chain atoms, especially methyl, which can be functionalised, any amino acid side chain, such as alanine, phenylalanine, valine and glutamic acid, a 4 to 7 membered heterocyclic ring optionally containing 1 or 2 N, S, O or P atoms or a 5 or 6 membered aromatic ring, optionally containing 1 or 2 N, O or S atoms which may be fused to another ring or a said alkyl chain substituted by a said aromatic ring, such as aryloxy alkyl, $A^1$ is $CH_2$ or O, and each of $R^2$ and $R^3$ is independently be H, OH, a branched or straight $C_1$ to $C_6$ alkyl chain optionally containing 1 or more eg. 2 N, S, O or P chain atoms which can be functionalised, optionally with 1, 2, 3, 4 or 5 halo substitutions, a 4 to 7 membered heterocyclic ring optionally containing 1 or 2 N, S, O or P atoms, or a 5 or 6 membered aromatic ring, optionally containing 1 or 2 N, O or S atoms which may be fused to another ring or a said alkyl chain substituted by a said aromatic ring,

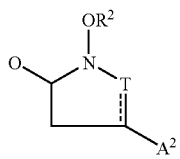
(B)

wherein $R^2$ is as defined above, - - - is a single bond and T is $CH_2$ or C=O, or - - - is a double bond and T is CH; $A^2$ is H or —$XCO_2R^4$; X is a single bond or a branched or straight $C_1$ to $C_6$ alkyl chain, optionally containing 1 or more eg. 2 N, S, O or P chain atoms and optionally substituted by eg. halo, OH, $NHR^2$ or $NHCOR^4$ where $R^2$ and $R^4$ are as defined above and $R^4$ represents H, a branched or straight chain $C_1$ to $C_6$ alkyl group optionally containing 1 or more eg. 2 N, S, O or P chain atoms, a 4 to 7 membered heterocyclic ring, optionally containing 1 or 2 N, S, O or P atoms, or a 5 or 6 membered aromatic ring, optionally containing 1 or 2 N, O or S atoms, which may be fused to another ring, or a salt thereof,

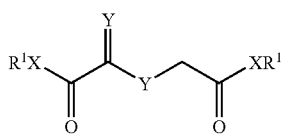
(C)

where each X which may be the same or different is NH, NR'', where R'' is OH, a branched or straight $C_1$ to $C_6$ alkyl chain optionally containing 1 or more eg. 2 N, S, O or P chain atoms which can be functionalised, or O i.e. $XR^1$ is typically OH or O-alkyl having a branched or straight $C_1$ to $C_6$ alkyl chain, especially MeO, each Y, which may be the same or different, is O or S and each $R^1$, which may be the same or different, is as defined above,

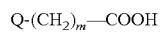
(D)

where m is 0 or 1, Q represents $(R^1R^6)_xZ$ where x is 0, 1 or 2, $R^1$ is as defined above and $R^6$ is as defined for $R^1$, and Z is P=$O(OH)_2$, $B(OH)_2$ or $SO_3H$, or a salt thereof, typically a sodium salt, or

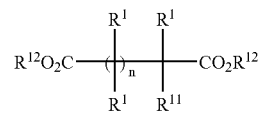
(E)

where each $R^1$, which are the same or different, is as defined above; $R^{11}$ represents OH or $R^{10}$ NH where $R^{10}$ is HO, $R^1CO$ or $HOOC(X)_x$ wherein $R^1$ is as defined above, x is 0 or 1 and X is $R^1R^1C$ wherein each $R^1$, which are the same or different, is as defined above; or $R^{10}$ is an amino acid residue $H_2N$ $(R^1R^1C)CO$— wherein each $R^1$, which are the same or different, is as defined above; n is 1 or 2 and $R^{12}$ is H or straight or branched $C_1$ to $C_6$ alkyl; or a salt thereof. Typically X is $CH_2$ or CHOH.

Another aspect of the invention concerns analogues of 2-oxoglutarate that act as improved (relative to 2-oxoglutarate) co-substrates for the HIF hydroxylases. Such a compound is 3-fluoro 2-oxoglutarate. Assays in which this compound replaces 2-oxoglutarate demonstrate a higher level of HIF hydroxylation than observed when using 2-oxoglutarate under analogous conditions.

These analogues possess the formula:

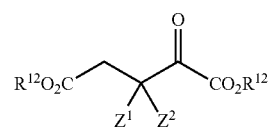
(F)

wherein each of $Z^1$ and $Z^2$ is independently hydrogen, SH or an electron withdrawing group such as halogen, preferably fluorine, or alkoxy such as methoxy, and $R^{12}$ is as defined above, or a salt thereof. Preferably one of $Z^1$ and $Z^2$ is hydrogen and the other is fluorine (3-F-2-OG).

Accordingly the present invention provides a compound of formula (A) to (F) for use in the treatment of a condition associated with increased or decreased HIF levels or activity, or a condition in which an increase or decrease in HIF levels or activity may be beneficial, as well as the use of a compound of formula (A) to (F) in the manufacture of a medicament for the treatment of such a condition.

The said alkyl groups and chains are typically functionalised by alcohol, fluorine, thiol, a carboxylic acid, phosphonic or phosphinic acid, sulphonic acid or other chelating group, in the case of the chains typically via an alkyl group.

In the formulae described herein, a branched or straight $C_1$ to $C_6$ alkyl chain may be a methyl, ethyl, propyl, butyl, iso-butyl, tert-butyl, pentyl, neopentyl, tert-pentyl or a primary, secondary or tertiary hexyl group. Hetero atoms such as O, S, N and P may replace one or more of the carbon atoms. Preferably the alkyl groups are methyl, the preferred heterocyclic rings are pyrolidine and tetrahydropyran and the preferred aromatic rings are benzene, naphthalene and pyridine.

Typically, each of $R^1$ and $R^5$ is independently H, OH, a branched or straight $C_1$ to $C_6$ alkyl chain optionally containing 1 or more N, S, O or P chain atoms, which can be functionalised, any amino acid side chain, a 4 to 7 membered heterocyclic ring optionally containing 1 or 2 N, S, O or P atoms or a 5 or 6 membered aromatic ring, optionally containing 1 or 2 N, O or S atoms which may be fused to another ring or a said alkyl chain substituted by a said aromatic ring.

Typically, $A^1$ is $CH_2$.

Typically, $A^2$ is $—XCO_2R^4$.

Typically, $R^{11}$ represents $R^{10}$ NH where $R^{10}$ is $R^1CO$ or $HOOC(X)_x$ wherein $R^1$ is as defined above, x is 0 or 1 and X is $R^1R^1C$ wherein each $R^1$, which are the same or different, is as defined above; or $R^{10}$ is an amino acid residue $H_2N(R^1R^1C)CO—$ wherein each $R^1$, which are the same or different, is as defined above.

Typically, each of $Z^1$ and $Z^2$ is independently hydrogen or an electron withdrawing group.

Typically, in the compounds of formula (F), $R^{12}$ is H. Alternatively, $R^{12}$ may be straight or branched $C_1$ to $C_6$ alkyl.

The compounds of formula (A) are hydroxamates. Preferred compounds include those where $R^5$ is aryloxyalkyl, especially oxyloxymethyl such as phenyloxymethyl or phenylalkyloxymethyl, especially benzyloxymethyl or substituted benzyloxymethyl such as p-hydroxy benzyloxymethyl and/or where $R^2$ and/or $R^3$ is $HOCH_2$.

Typical compounds include N-phenoxy-acetyl-(L)-alanine-hydroxamide (Is41) and the corresponding (D) isomer (Is43) as well as the corresponding tyrosine derivatives (Is44 and 45) and L- and D-phenylglycine derivatives (Is46 and 47), along with benzo hydroxamic acid and N-phenoxy-acetyl-D-phenylalanine hydroxamic acid (Is42).

These compounds can generally be prepared following the method of Walter et al., Tetrahedron 1997, 53, 7275-7290 and Biorg. Chem 1999, 27, 35-40.

The compounds of formula (B) are cyclic hydroxamates. Preferred compounds are those where X is a single bond or methyl and/or $R^2$ is H or phenylalkyl, especially benzyl and/or $R^4$ is H or methyl. Typical compounds include (1-hydroxy-2,5-dioxo-pyrrolidin-3-yl) acetic acid (Is52), (1-hydroxy-2,5-dioxo-pyrrolidin-3-yl) carboxylic acid (ANU 2) and its N-benzoyloxy derivative (ANU 1) along with (1-benzyloxy-2,5-dioxo-pyrrolidin-3-yl) acetic acid (Is50) and the corresponding methyl ester (Is64), and N-hydroxy succinimide (C1). Note that Is52 ($R^2$=H, T=C=O, X=$CH_2R^4$=H) is highly active reflecting its structural analogy with 2-oxoglutarate. These compounds can be prepared using the general procedure of Schlicht et al. (U.S. Pat. No. 4,446,038).

The compounds of formula (C) are analogues of 2-oxoglutarate or oxalyl derivatives of hydroxyacetate and mercapto acetic acid. Preferred compounds include those where X is O and/or $R^1$ is H or methyl. Typical compounds include dimethyl oxalylglycolate (Is10) as well as its free acid (Is14) and dimethyl oxalylthioglycolate (Is11). These compounds can be prepared following Franklin et al., J. Med. Chem 1992, 35, 2652-2658 or Kwon et al., J. Am. Chem. Soc. 1989, 111, 1854-1860.

The compounds of formula (D) are carboxylic acids which possess a phosphonic, sulphonic or boronic acid group as well as salts of these. Typically R' and $R^6$ are hydrogen. Preferred compounds include the phosphoric acids where x is 0, 1 or 2 (C3, 4 and 5, respectively) as well as disodium 3-sulpho-propionate (Is63) and its free acid, and 3-borono-propionic acid (Is62).

The compounds of formula (E) are N-acylated amino acids or polycarboxylic acids. Typical compounds are those where $R^1$ is H, and/or $R^{12}$ is H or ethyl. When $R^{11}$ represents $R^{10}NH$ the compounds are typically dipeptides such that $R^{10}$ is an acyl group of a natural amino acid such as glycine. Typical preferred such compounds include Asp-Gly (C18), cyclo (Asp-Gly) (C19), beta-Asp-Gly (C20), Glu-Gly (C21) and Z-Glu-Gly (C22). Other typical compounds include those where $R^{10}$ is acetyl or benzoyl such as the N-acetylated derivatives of L-aspartic acid (C6) and of L-glutamic acid (C7) i.e. $R^{10}$ is acetyl and N-benzoylated derivatives of glutamic acid (C15 and Is90) i.e. $R^{10}$ is benzoyl. Other typical compounds include those where $R^{11}$ is $—NHOH$ such as diethyl 2-(hydroxylamino)-glutarate (Is51 being the racemic form of this compound) and those where $R^{11}$ is OH such as 2-hydroxyglutaric acid (Is57). When $R^{11}$ is $HOOC(X)_x$, X is especially $CH^2$ or CHOH. The compounds are typically citric acid (C12), tricarballylic acid (C13) and succinic acid as well as the tri-methyl ester of ethane tricarboxylic acid (Is72).

The compounds of formula (F) are analogues of 2-oxoglutarate. Preferred compounds include 3-fluoro-2-oxoglutarate compounds (i.e. $Z^1$ is H and $Z^2$ is F) such as 3-fluoro-2-oxoglutaric acid (Is18) and the corresponding dimethyl ester (Is19).

The compounds which are acids can be present in the form of salts, such as sodium salts.

For therapeutic treatment, the compound may be used in combination with any other active substance, e.g. for anti-tumour therapy another anti-tumour compound or therapy, such as radiotherapy or chemotherapy.

Generally, the modulator is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent. As noted below, a composition according to the present invention may include in addition to a modulator compound as disclosed, one or more other molecules of therapeutic use, such as an anti-tumour agent.

In general they take the form of compositions wherein the compound is in a mixture with a pharmaceutically acceptable carrier or diluent. The carrier may be liquid, e.g. saline, ethanol, glycerol and mixtures thereof, or solid, e.g. in the form of a tablet, or in a semi-solid form such as a gel formulated as a depot formulation or in a transdermally administerable vehicle, such as a transdermal patch. The modulator compound or composition comprising it may be formulated as the coating of a coated stent.

The invention further provides a method of treatment which includes administering to a patient compound as defined above. Exemplary purposes of such treatment are discussed elsewhere herein.

The therapeutic/prophylactic purpose of such a method or use may be the modulation of the level of HIFα in a cell by modulation, e.g. disruption or interference, of the hydroxylation of HIFα, which may occur for example at proline 402, 564 or other proline residue. Hydroxylation of HIFα promotes pVHL binding which leads to ubiquitin dependent proteolysis of HIFα as described above.

The therapeutic/prophylactic purpose may be related to the treatment of a condition associated with reduced or suboptimal or increased HIF levels or activity, or conditions where an alteration in HIF levels or activity may be beneficial such as:

(i) ischaemic conditions, for example organ ischaemia, including coronary, cerebrovascular and peripheral vascular insufficiency. The therapy may be applied in two ways; following declared tissue damage, e.g. myocardial infarction (in order to limit tissue damage), or prophylactically to prevent or ameliorate ischaemia, e.g. promotion of coronary collaterals in the treatment of angina.

(ii) wound healing and organ regeneration.

(iii) auto-, allo-, and xeno-transplantation.

(iv) systemic blood pressure.

(v) cancer; HIFα is commonly up-regulated in tumour cells and has major effects on tumour growth and angiogenesis.

(vi) inflammatory disorders.

(vii) pulmonary arterial blood pressure, neurodegenerative disease.

(viii) metabolic disorders, e.g. diabetes.

Modulating HIF prolyl hydroxylase activity in a person, an organ, or a group of cells may be exploited in different ways to obtain a therapeutic benefit:

(a) Non cell autonomous: The HIF system is used by cells to influence the production of substances which signal to other cells. These signals may then have effects at (i) a distant site (for example erythropoietin acts on the bone marrow) or (ii) locally (angiogenic growth factors increase the local formation of blood vessels). Manipulating non cell autonomous behaviour via altering hydroxylase activity is therefore useful in the treatment of anaemia, and local ischaemia, for example in the eye, brain, heart and limbs. Many other signals that are involved in aspects of physiological homeostasis may be, or are known to be, adjusted by HIF activation. Consequently altering HIF prolyl hydroxylase activity may be used to potentiate or initiate a helpful response for a therapeutic benefit, or to prevent or ameliorate a harmful response. For example, this approach can be used to alter appetite, or blood pressure in the systemic or pulmonary beds. (b) Cell autonomous: the HIF system is also used by cells to regulate cellular metabolism, and decisions concerning differentiation, proliferation and apoptosis. Therefore manipulating the HIF system can be used to alter the viability and behaviour of cells. An increase in cell viability can be achieved by increasing HIF activation, for example in an ischaemic tissue. This approach can also be used in improving pancreatic beta cell viability as a way of ameliorating diabetes, or of improving the viability or function of a group or groups of neurons in Parkinson's disease, motorneurone disease or forms of dementia. In a different approach, the HIF signal can be manipulated to prevent a group of cells proliferating, or to promote its death or differentiation. For example transient activation of the HIF system in a malignant tumour can be used to provoke death of a substantial number of tumour cells.

Pharmaceutical Compositions

In various further aspects, the present invention thus provides a pharmaceutical composition, medicament, drug or other composition for such a purpose, the composition comprising one or more compounds of formulae (A) to (F), or derivatives thereof, the use of such an composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

The agent may be used as sole active agent or in combination with one another or with any other active substance, e.g. for anti-tumour therapy another anti-tumour compound or therapy, such as radiotherapy or chemotherapy.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous. The compositions will typically be sterile.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

The following Examples further illustrate the present invention.

EXAMPLE 1

Figure 2:
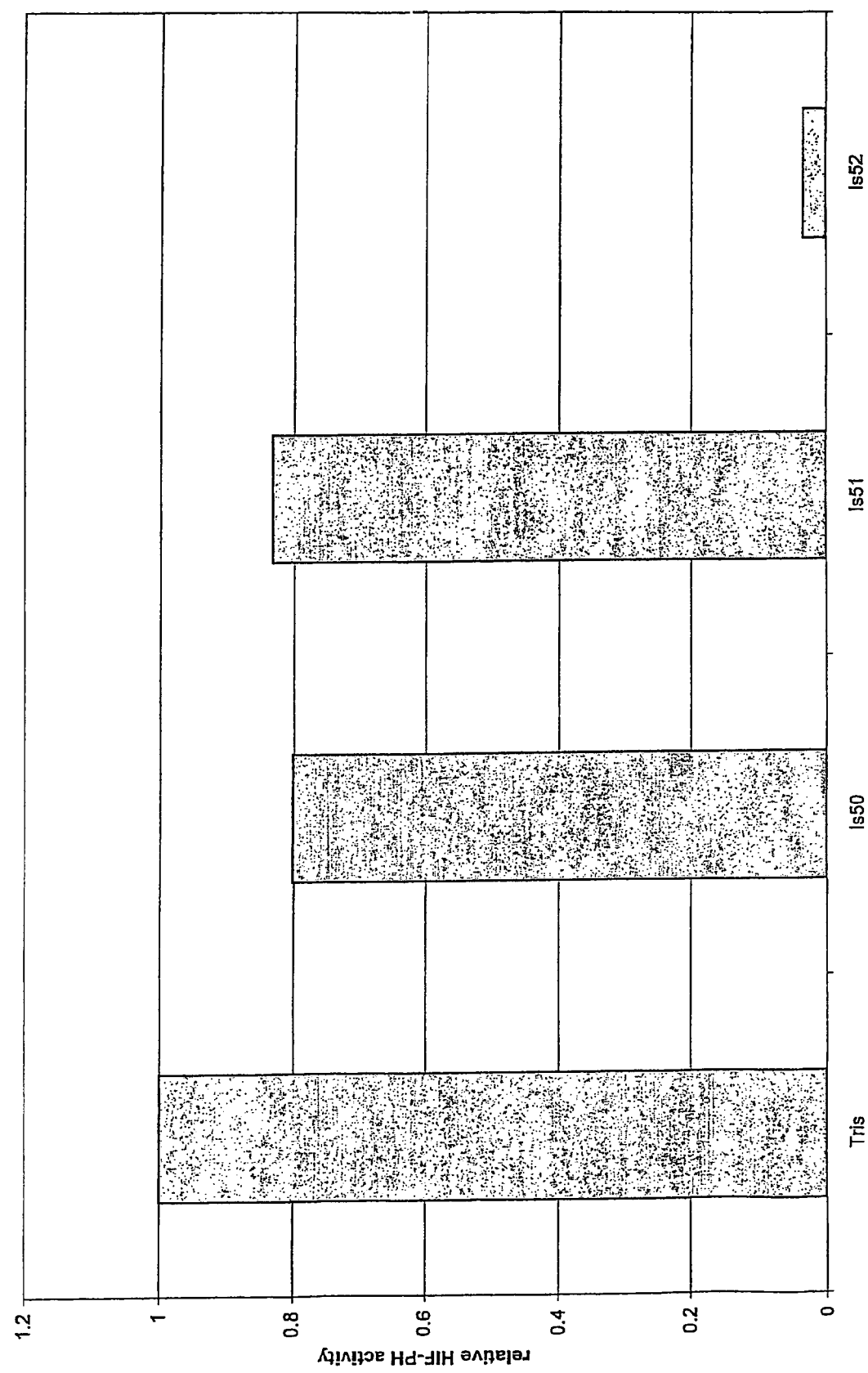
Figure 3:
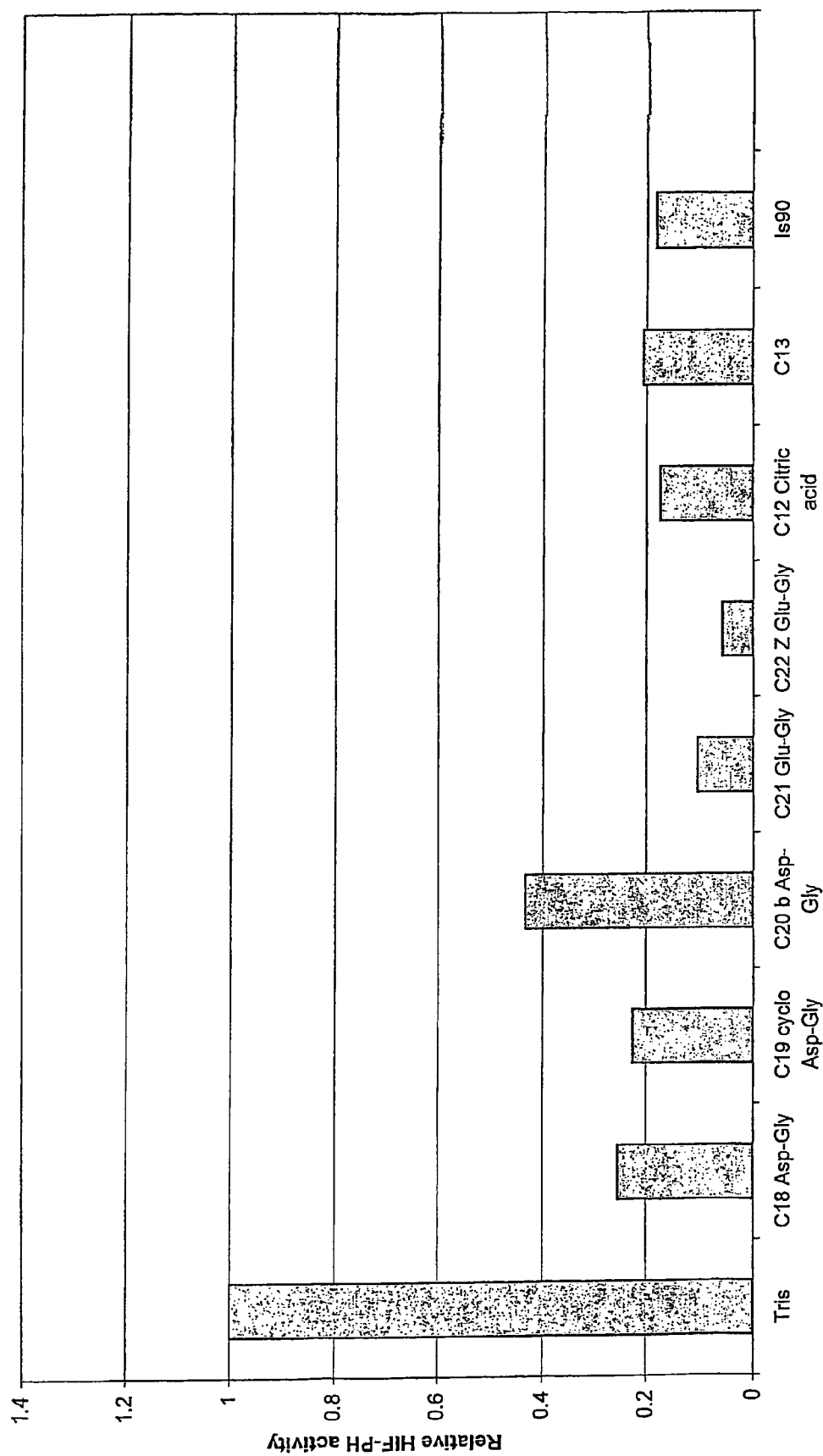
Figure 4:
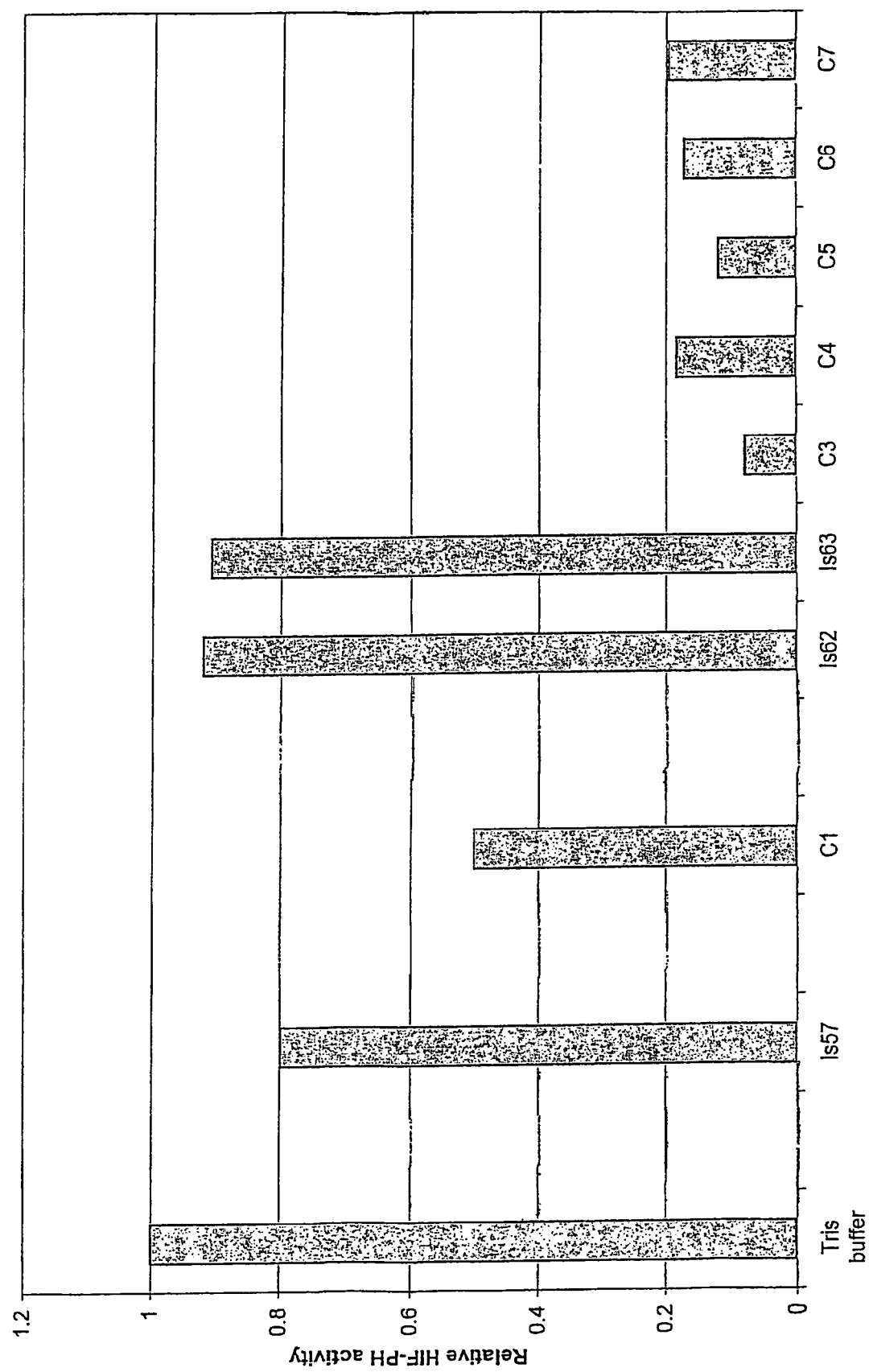
Figure 5:
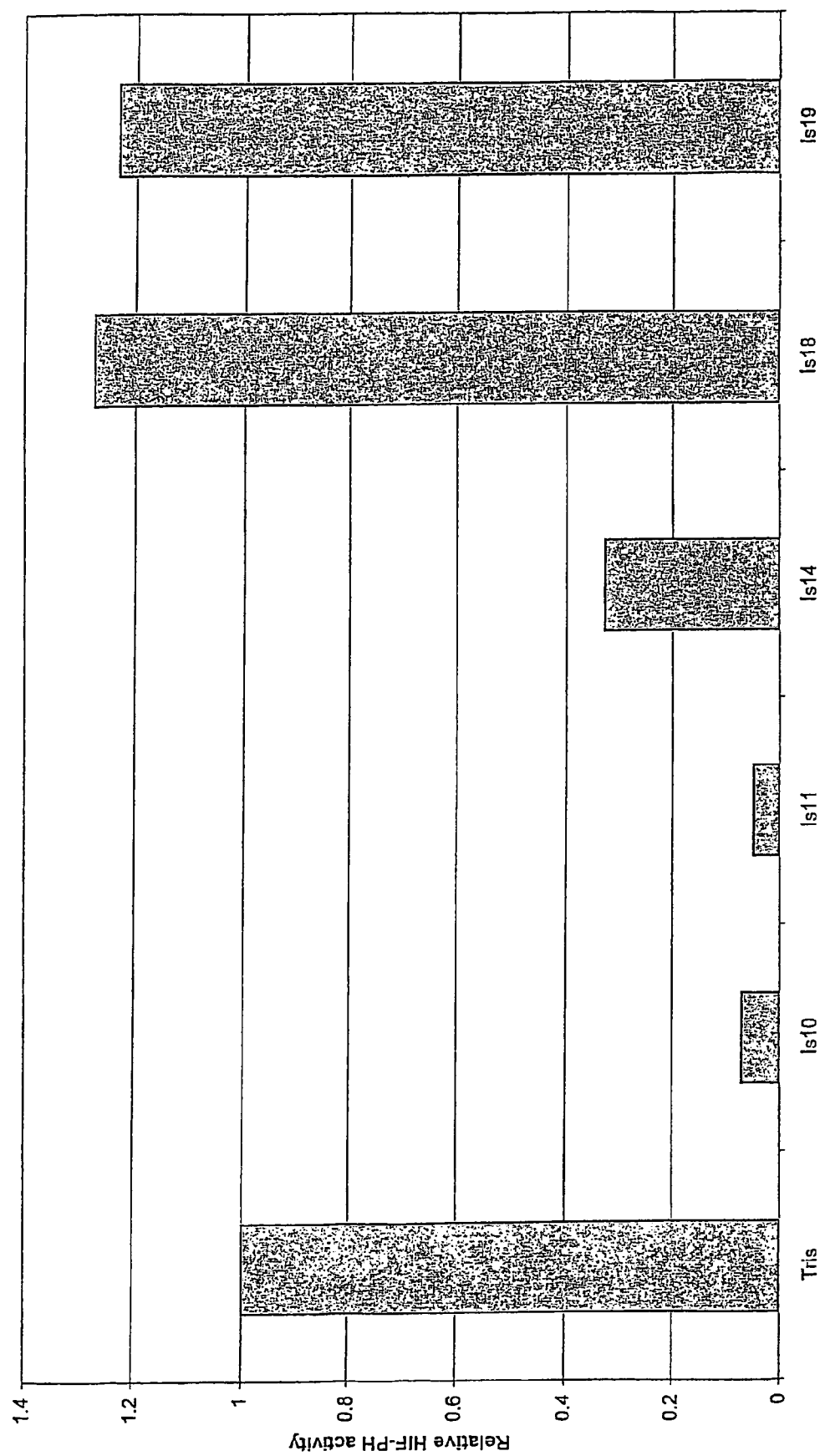

In vitro screening of potential inhibitors of HIF modification was performed using a capture assay. A Gal/HIF-1α/VP16 fusion protein expressing HIF-1α residues 549-582 was prepared by IVTT (see British Application No. 0118952.1) and used as a substrate in the assay. The unlabelled substrate was immunopurified on beads, washed, and aliquots incubated in the presence of RCC4 cell extract, with 100 μM FeCl$_2$ and 2 mM of the potential inhibitor. The inhibitors were either dissolved in DMSO or Tris as indicated. Controls, where no inhibitor but the equivalent amount of DMSO or Tris was added, were also performed. After washing, the beads were assayed for their ability to interact with 35-S labelled pVHL IVTT. Hydroxylation of the fusion protein by HIF hydroxylase present in the cell extract leads to the ability to capture the labelled pVHL and the amount of labelled protein bound to the fusion protein can then be measured to determine relative HIF hydroxylase activity. FIGS. 1 to 5 show HIF hydroxylase activity in the presence of a particular inhibitor relative to that seen in the absence of the inhibitor (the DMSO/Tris control).

The invention claimed is:

1. A method of modulating inhibiting HIF prolyl hydroxylase activity in a subject comprising administering to a subject at least one compound according of formula (E) or a salt thereof:

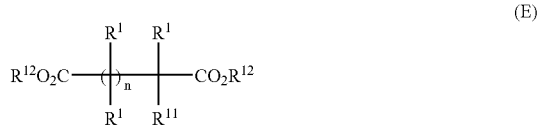

wherein each $R^1$, which are the same or different, is independently H, or OH;

$R^{11}$ represents $R^{10}NH$, where $R^{10}$ is HO, $R^1CO$ wherein $R^1$ is as defined above, an acyl group of a natural amino acid, acetyl or benzoyl;

n is 1 or 2; and $R^{12}$ is H or straight or branched $C_1$ to $C_6$ alkyl; wherein the compound is not citric acid or isocitric acid; and wherein HIF α levels are increased in the subject.

2. The method according to claim 1, wherein $R^1$ is H and $R^{12}$ is H or ethyl.

3. The method according to claim 1, wherein $R^{11}$ is NHOH.

* * * * *

SEQUENCE LISTING

```
<160> NUMBER OF SEQ ID NOS: 6

<210> SEQ ID NO 1
<211> LENGTH: 2110
<212> TYPE: DNA
<213> ORGANISM: Homo sapiens
<220> FEATURE:
<221> NAME/KEY: CDS
<222> LOCATION: (297)..(1517)

<400> SEQUENCE: 1
gctttcccct gcctgcctgt ctctagtttc tctcacatcc cttttttttt tcctttctct      60
agccaccctg aagggtccct tcccaagccc ttagggaccg cagaggactt ggggaccagc     120 aagcaaccccc cagggcacga aagagctct tgctgtctgc cctgcctcac cctgccccac     180
accaggcccg gtggccccca gctgcatcaa gtggaggcgg aggaggaggc ggaggagggt     240
ggcaccatgg gcccgggcgg tgccctccat gcccggggga tgaagacact gctgcc atg     299
                                                                    Met
                                                                      1 gac agc ccg tgc cag ccg cag ccc cta agt cag gct ctc cct cag tta        347
Asp Ser Pro Cys Gln Pro Gln Pro Leu Ser Gln Ala Leu Pro Gln Leu
              5                  10                  15 cca ggg tct tcg tca gag ccc ttg gag cct gag cct ggc cgg gcc agg        395
Pro Gly Ser Ser Ser Glu Pro Leu Glu Pro Glu Pro Gly Arg Ala Arg
         20                  25                  30 atg gga gtg gag agt tac ctg ccc tgt ccc ctg ctc ccc tcc tac cac        443
Met Gly Val Glu Ser Tyr Leu Pro Cys Pro Leu Leu Pro Ser Tyr His
     35                  40                  45

tgt cca gga gtg cct agt gag gcc tcg gca ggg agt ggg acc ccc aga        491
Cys Pro Gly Val Pro Ser Glu Ala Ser Ala Gly Ser Gly Thr Pro Arg
 50                  55                  60                  65 gcc aca gcc acc tct acc act gcc agc cct ctt cgg gac ggt ttt ggc        539
Ala Thr Ala Thr Ser Thr Thr Ala Ser Pro Leu Arg Asp Gly Phe Gly
                 70                  75                  80 ggg cag gat ggt ggt gag ctg cgg ccg ctg cag agt gaa ggc gct gca        587
Gly Gln Asp Gly Gly Glu Leu Arg Pro Leu Gln Ser Glu Gly Ala Ala
             85                  90                  95 gcg ctg gtc acc aag ggg tgc cag cga ttg gca gcc cag ggc gca cgg        635
Ala Leu Val Thr Lys Gly Cys Gln Arg Leu Ala Ala Gln Gly Ala Arg
        100                 105                 110 cct gag gcc ccc aaa cgg aaa tgg gcc gag gat ggt ggg gat gcc cct        683
Pro Glu Ala Pro Lys Arg Lys Trp Ala Glu Asp Gly Gly Asp Ala Pro
    115                 120                 125

tca ccc agc aaa cgg ccc tgg gcc agg caa gag aac cag gag gca gag        731
Ser Pro Ser Lys Arg Pro Trp Ala Arg Gln Glu Asn Gln Glu Ala Glu
130                 135                 140                 145
```

| | |
|---|---|
| cgg gag ggt ggc atg agc tgc agc tgc agc agt ggc agt ggt gag gcc<br>Arg Glu Gly Gly Met Ser Cys Ser Cys Ser Ser Gly Ser Gly Glu Ala<br>150 155 160 | 779 |
| agt gct ggg ctg atg gag gag gcg ctg ccc tct gcg ccc gag cgc ctg<br>Ser Ala Gly Leu Met Glu Glu Ala Leu Pro Ser Ala Pro Glu Arg Leu<br>165 170 175 | 827 |
| gcc ctg gac tat atc gtg ccc tgc atg cgg tac tac ggc atc tgc gtc<br>Ala Leu Asp Tyr Ile Val Pro Cys Met Arg Tyr Tyr Gly Ile Cys Val<br>180 185 190 | 875 |
| aag gac agc ttc ctg ggg gca gca ctg ggc ggt cgc gtg ctg gcc gag<br>Lys Asp Ser Phe Leu Gly Ala Ala Leu Gly Gly Arg Val Leu Ala Glu<br>195 200 205 | 923 |
| gtg gag gcc ctc aaa cgg ggt ggg cgc ctg cga gac ggg cag cta gtg<br>Val Glu Ala Leu Lys Arg Gly Gly Arg Leu Arg Asp Gly Gln Leu Val<br>210 215 220 225 | 971 |
| agc cag agg gcg atc ccg ccg cgc agc atc cgt ggg gac cag att gcc<br>Ser Gln Arg Ala Ile Pro Pro Arg Ser Ile Arg Gly Asp Gln Ile Ala<br>230 235 240 | 1019 |
| tgg gtg gaa ggc cat gaa cca ggc tgt cga agc att ggt gcc ctc atg<br>Trp Val Glu Gly His Glu Pro Gly Cys Arg Ser Ile Gly Ala Leu Met<br>245 250 255 | 1067 |
| gcc cat gtg gac gcc gtc atc cgc cac tgc gca ggg cgg ctg ggc agc<br>Ala His Val Asp Ala Val Ile Arg His Cys Ala Gly Arg Leu Gly Ser<br>260 265 270 | 1115 |
| tat gtc atc aac ggg cgc acc aag gcc atg gtg gcg tgt tac cca ggc<br>Tyr Val Ile Asn Gly Arg Thr Lys Ala Met Val Ala Cys Tyr Pro Gly<br>275 280 285 | 1163 |
| aac ggg ctc ggg tac gta agg cac gtt gac aat ccc cac ggc gat ggg<br>Asn Gly Leu Gly Tyr Val Arg His Val Asp Asn Pro His Gly Asp Gly<br>290 295 300 305 | 1211 |
| cgc tgc atc acc tgt atc tat tac ctg aat cag aac tgg gac gtt aag<br>Arg Cys Ile Thr Cys Ile Tyr Tyr Leu Asn Gln Asn Trp Asp Val Lys<br>310 315 320 | 1259 |
| gtg cat ggc ggc ctg ctg cag atc ttc cct gag ggc cgg ccc gtg gta<br>Val His Gly Gly Leu Leu Gln Ile Phe Pro Glu Gly Arg Pro Val Val<br>325 330 335 | 1307 |
| gcc aac atc gag cca ctc ttt gac cgg ttg ctc att ttc tgg tct gac<br>Ala Asn Ile Glu Pro Leu Phe Asp Arg Leu Leu Ile Phe Trp Ser Asp<br>340 345 350 | 1355 |
| cgg cgg aac ccc cac gag gtg aag cca gcc tat gcc acc agg tac gcc<br>Arg Arg Asn Pro His Glu Val Lys Pro Ala Tyr Ala Thr Arg Tyr Ala<br>355 360 365 | 1403 |
| atc act gtc tgg tat ttt gat gcc aag gag cgg gca gca gcc aaa gac<br>Ile Thr Val Trp Tyr Phe Asp Ala Lys Glu Arg Ala Ala Ala Lys Asp<br>370 375 380 385 | 1451 |
| aag tat cag cta gca tca gga cag aaa ggt gtc caa gta cct gta tca<br>Lys Tyr Gln Leu Ala Ser Gly Gln Lys Gly Val Gln Val Pro Val Ser<br>390 395 400 | 1499 |
| cag ccg cct acg ccc acc tagtggccag tcccagagcc gcatggcaga<br>Gln Pro Pro Thr Pro Thr<br>405 | 1547 |
| cagcttaaat gacttcagga gagccctggg cctgtgctgg ctgctccttc cctgccaccg | 1607 |
| ctgctgcttc tgactttgcc tctgtcctgc ctggtgtgga gggctctgtc tgttgctgag | 1667 |
| gaccaaggag gagaagagac ctttgctgcc ccatcatggg ggctgggggtt gtcacctgga | 1727 |
| cagggggcag ccgtggaggc caccgttacc aactgaagct gggggcctgg gtcctaccct | 1787 |
| gtctggtcat gaccccatta ggtatggaga gctgggagga ggcattgtca cttcccacca | 1847 |

-continued

```
ggatgcagga cttggggttg aggtgagtca tggcctcttg ctggcaatgg ggtgggagga    1907 gtaccccaa gtcctctcac tcctccagcc tggaatgtga agtgactccc caaccccttt    1967
ggccatggca ggcaccttt ggactgggct gccactgctt gggcagagta aaaggtgcca    2027
ggaggagcat gggtgtggaa gtcctgtcag ccaagaaata aagtttacc tcagagctgc    2087 aaaaaaaaaa aaaaaaaaa aaa                                            2110
```

<210> SEQ ID NO 2
<211> LENGTH: 407
<212> TYPE: PRT
<213> ORGANISM: Homo sapiens

<400> SEQUENCE: 2

```
Met Asp Ser Pro Cys Gln Pro Gln Pro Leu Ser Gln Ala Leu Pro Gln
 1               5                  10                  15

Leu Pro Gly Ser Ser Glu Pro Leu Glu Pro Glu Pro Gly Arg Ala
            20                  25                  30

Arg Met Gly Val Glu Ser Tyr Leu Pro Cys Pro Leu Leu Pro Ser Tyr
        35                  40                  45

His Cys Pro Gly Val Pro Ser Glu Ala Ser Ala Gly Ser Gly Thr Pro
    50                  55                  60

Arg Ala Thr Ala Thr Ser Thr Thr Ala Ser Pro Leu Arg Asp Gly Phe
65                  70                  75                  80

Gly Gly Gln Asp Gly Gly Glu Leu Arg Pro Leu Gln Ser Glu Gly Ala
                85                  90                  95

Ala Ala Leu Val Thr Lys Gly Cys Gln Arg Leu Ala Ala Gln Gly Ala
            100                 105                 110

Arg Pro Glu Ala Pro Lys Arg Lys Trp Ala Glu Asp Gly Gly Asp Ala
        115                 120                 125

Pro Ser Pro Ser Lys Arg Pro Trp Ala Arg Gln Glu Asn Gln Glu Ala
    130                 135                 140

Glu Arg Glu Gly Gly Met Ser Cys Ser Cys Ser Ser Gly Ser Gly Glu
145                 150                 155                 160

Ala Ser Ala Gly Leu Met Glu Glu Ala Leu Pro Ser Ala Pro Glu Arg
                165                 170                 175

Leu Ala Leu Asp Tyr Ile Val Pro Cys Met Arg Tyr Tyr Gly Ile Cys
            180                 185                 190

Val Lys Asp Ser Phe Leu Gly Ala Ala Leu Gly Gly Arg Val Leu Ala
        195                 200                 205

Glu Val Glu Ala Leu Lys Arg Gly Gly Arg Leu Arg Asp Gly Gln Leu
    210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
            260                 265                 270

Ser Tyr Val Ile Asn Gly Arg Thr Lys Ala Met Val Ala Cys Tyr Pro
        275                 280                 285

Gly Asn Gly Leu Gly Tyr Val Arg His Val Asp Asn Pro His Gly Asp
    290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
```

-continued

```
            325                 330                 335
Val Ala Asn Ile Glu Pro Leu Phe Asp Arg Leu Leu Ile Phe Trp Ser
        340                 345                 350

Asp Arg Arg Asn Pro His Glu Val Lys Pro Ala Tyr Ala Thr Arg Tyr
        355                 360                 365

Ala Ile Thr Val Trp Tyr Phe Asp Ala Lys Glu Arg Ala Ala Ala Lys
        370                 375                 380

Asp Lys Tyr Gln Leu Ala Ser Gly Gln Lys Gly Val Gln Val Pro Val
385                 390                 395                 400

Ser Gln Pro Pro Thr Pro Thr
                405

<210> SEQ ID NO 3
<211> LENGTH: 5163
<212> TYPE: DNA
<213> ORGANISM: Homo sapiens
<220> FEATURE:
<221> NAME/KEY: CDS
<222> LOCATION: (3157)..(4434)

<400> SEQUENCE: 3
ttaggggcag aaaaacattt gtaataatta atggctttga gagacacaag gctttgtttg      60
ccccagagta ttagttaacc cacctagtgc tcctaatcat acaatattaa ggattgggag     120
ggacattcat tgcctcactc tctatttgtt tcaccttctg taaaattggt agaataatag     180
tacccacttc atagcattgt atgatgatta aattggttaa tattttttaaa atgcttagaa    240 cacagattgg gcacataaca gcaagcacca catgtgttta taagataaat tcctttgtgt     300
tgccttccgt taaagtttaa ataagtaaat aaataaataa atacttgcat gacattttga     360
agtctctcta taacatctga gtaagtggcg gctgcgacaa tgctactgga gttccagaat     420
cgtgttggtg acaagattgt tcaccagcat atggtgtggt gaaaactcac taatttggaa     480
ttagttcaga ttattaagcc tgaataggtg aaaatcctga aatcaaggat ctttggaact     540
atttgaaatc agtattttat attttcctgt tgtattcatt aaagtgttgc aagtgttcta     600
tttgatggat taagtatatt taggatatac atgttcaatt tgtgattttg tatacttaat     660
tggaacaaga aagctaataa aggttttgat atggacatct attcttttaa gtaaacttca     720
atgaaaatat atgagtagag catatagaga tgtaaataat ttgtggacac accacagact     780
gaaatagcaa atttaaaaga aattgttgga agaatcaagt gtttgtggaa tgagtcctcc     840
tagtaaagtt cctgctcttg tgaataatta agcctcatgt ataattacta tagcaaaagg     900
aagcctaaga agtattagac tctacttgta tttaaattac atttttacata atttatgtgt    960 atgaaaaatg ttttaaatgc ttatttcgt aagccatgag atagctcctt tatattttaa    1020
gaatttctga attaatttgc ttggattta ttagtgcaaa tggcagagct agcaattcct     1080
ttttctgtgt tcccattcca tcctattcat ccctctttta ggaaactctg aactctggat    1140
tgtccttgtt tacatacctg cctcctgcat tggactatgt gtctctgagt gtagtatgac    1200
taattcattt gtttgtcaag gactctcaat gcatttgttg aacagcctaa ttagtaatgt    1260
ctgcaacaat gacattttac tgtatttaat aaagctctgg gaaagtagga tacacataag    1320
acaggtctag gtctaaattc tttacagaaa cttggatttt tagttcggtt tgaaatttga    1380
agatgtgagt atatttatct cagtttccca aaggacaagc taattggaat tatcatcctc    1440
tttcacttga ttggatcccc agaatgccat ttacgcatgc agcaggattt tataacagtt    1500
ttaaattctg tatatttgat gaagagggttt tatatttttg gattcaagcc tcttttaaa    1560
```

-continued

```
cttctacaat atggtttaca ataattcctt atatcctgct tttgaaatac atattacaac    1620
tttttaagtt tggaaggcta tatttcaagg actgaagtta cagtatactc aagtgataca    1680
caagcctagc accccacttt ccacatagtg ttcgataaag attgataaac tcgaaatcac    1740
agaccttta  attcttaaga caaatagcag cagaaagaaa catctttggc ttatttctgg    1800
taaggttttt atgctctgta aaacaaagaa ttgtattcat ccgcgcagca cagattctat    1860
taaaaataaa tgtgagagtc gttaatgtag tactgctcat ttaccatcaa aattcacttt    1920
tcaggaataa tcccatcagt ttaaattgga tattggaatg agcattgatt acatttaact    1980
tggtagccca aaatttcttc atggggtttt gaactcggcg ggatttcaaa ggttttaaaa    2040
atgagttttt gattttttt  aaaaccctca aatttcatta cctttaaact aggtcgaaac    2100
ggggcgcaag agattggatt aacaccatag taatacttat tttgttctta accatttcag    2160
ggcttcttga aatagaggct gtatggtgta atggaaaaaa cagccttgga atctgggagc    2220
ctgattcctg gattcagtcc cagttttgcg tgaccttggg caagttactt tacttctctg    2280
aatttccgtt tcctcctctg caaaatgagg atcgcaatag ccaccttgca acctgactg     2340
gagcgagcct cgcacacccc gcgccggcct ggaggaagag cagccatgat tacgccgcct    2400
tcgctccgct acccgcttgc ggctggcgcc ctcctccagc aggtgtaggc gctgccgcgc    2460
tgccccacgc ctttccgccg ctcgcgggcc tgcgcctcgg cgtccccgag gaggccgctg    2520
cgggctgagg tagcgcaccg gcctctcggt gtcccagtcc ggtcccgggc ggagggaaag    2580
cgggcgaccc acctccgagg cagaagccga ggcccggccc cgccgagtgc ggaggagcgc    2640
aggcagcccc cgcccctcgg ccctcccccc ggccctcccg gccctccctc cgcccccccc    2700
gccctcgcgc ccgccccgcc cgggtcgccg cggggccgtg tgtacgtgc  agagcgcgca    2760
gagcgagtgg cgcccgtatg ccctgcgctc ctccacagcc tgggccgggc cgcccgggac    2820
gctgaggcgc cggcggcggc cgagggggcc ggtcttgcgc tccccaggcc cgcgcgcctg    2880
agcccaggtt gccattcgcc gcacaggccc tattctctca gccctcggcg gcgatgaggc    2940
gctgaggcgc ctgccggcgc tgcgccggag cttaggactc ggaagcggcc gggccgaggg    3000
cgtggggtgc cggcctccct gaggcgaggg tagcgggtgc atggcgcagt aacggcccct    3060
atctctctcc ccgctcccca gcctcgggcg aggccgtccg gccgctaccc ctcctgctcg    3120
gccgccgcag tcgccgtcgc cgccgccgcc gccgcc atg gcc aat gac agc ggc    3174
                                        Met Ala Asn Asp Ser Gly
                                        1               5 ggg ccc ggc ggg ccg agc ccg agc gag cga gac cgg cag tac tgc gag    3222
Gly Pro Gly Gly Pro Ser Pro Ser Glu Arg Asp Arg Gln Tyr Cys Glu
         10                 15                  20 ctg tgc ggg aag atg gag aac ctg ctg cgc tgc agc cgc tgc cgc agc    3270
Leu Cys Gly Lys Met Glu Asn Leu Leu Arg Cys Ser Arg Cys Arg Ser
     25                  30                  35 tcc ttc tac tgc tgc aag gag cac cag cgt cag gac tgg aag aag cac    3318
Ser Phe Tyr Cys Cys Lys Glu His Gln Arg Gln Asp Trp Lys Lys His
 40                  45                  50 aag ctc gtg tgc cag ggc agc gag ggc gcc ctc ggc cac gga gtg ggc    3366
Lys Leu Val Cys Gln Gly Ser Glu Gly Ala Leu Gly His Gly Val Gly
 55                  60                  65                  70 cca cac cag cat tcc ggc ccc gcg ccg ccg gct gca gtg ccg ccg ccc    3414
Pro His Gln His Ser Gly Pro Ala Pro Pro Ala Ala Val Pro Pro Pro
             75                  80                  85 agg gcc ggg gcc cgg gag ccc agg aag gca gcg gcg cgc cgg gac aac    3462
Arg Ala Gly Ala Arg Glu Pro Arg Lys Ala Ala Ala Arg Arg Asp Asn
```

```
                        90                      95                     100
gcc tcc ggg gac gcg gcc aag gga aaa gta aag gcc aag ccc ccg gcc          3510
Ala Ser Gly Asp Ala Ala Lys Gly Lys Val Lys Ala Lys Pro Pro Ala
            105                     110                     115 gac cca gcg gcg gcc gcg tcg ccg tgt cgt gcg gcc gcc ggc ggc cag          3558
Asp Pro Ala Ala Ala Ala Ser Pro Cys Arg Ala Ala Ala Gly Gly Gln
        120                     125                     130 ggc tcg gcg gtg gct gcc gaa gcc gag ccc ggc aag gag gag ccg ccg          3606
Gly Ser Ala Val Ala Ala Glu Ala Glu Pro Gly Lys Glu Glu Pro Pro
135                     140                     145                     150 gcc cgc tca tcg ctg ttc cag gag aag gcg aac ctg tac ccc cca agc          3654
Ala Arg Ser Ser Leu Phe Gln Glu Lys Ala Asn Leu Tyr Pro Pro Ser
                    155                     160                     165 aac acg ccc ggg gat gcg ctg agc ccc ggc ggc ggc ctg cgg ccc aac          3702
Asn Thr Pro Gly Asp Ala Leu Ser Pro Gly Gly Gly Leu Arg Pro Asn
                170                     175                     180 ggg cag acg aag ccc ctg ccg gcg ctg aag ctg gcg ctc gag tac atc          3750
Gly Gln Thr Lys Pro Leu Pro Ala Leu Lys Leu Ala Leu Glu Tyr Ile
            185                     190                     195 gtg ccg tgc atg aac aag cac ggc atc tgt gtg gtg gac gac ttc ctc          3798
Val Pro Cys Met Asn Lys His Gly Ile Cys Val Val Asp Asp Phe Leu
        200                     205                     210 ggc aag gag acc gga cag cag atc ggc gac gag gtg cgc gcc ctg cac          3846
Gly Lys Glu Thr Gly Gln Gln Ile Gly Asp Glu Val Arg Ala Leu His
215                     220                     225                     230 gac acc ggg aag ttc acg gac ggg cag ctg gtc agc cag aag agt gac          3894
Asp Thr Gly Lys Phe Thr Asp Gly Gln Leu Val Ser Gln Lys Ser Asp
                    235                     240                     245 tcg tcc aag gac atc cga ggc gat aag atc acc tgg atc gag ggc aag          3942
Ser Ser Lys Asp Ile Arg Gly Asp Lys Ile Thr Trp Ile Glu Gly Lys
                250                     255                     260 gag ccc ggc tgc gaa acc att ggg ctg ctc atg agc agc atg gac gac          3990
Glu Pro Gly Cys Glu Thr Ile Gly Leu Leu Met Ser Ser Met Asp Asp
            265                     270                     275 ctg ata cgc cac tgt aac ggg aag ctg ggc agc tac aaa atc aat ggc          4038
Leu Ile Arg His Cys Asn Gly Lys Leu Gly Ser Tyr Lys Ile Asn Gly
        280                     285                     290 cgg acg aaa gcc atg gtt gct tgt tat ccg ggc aat gga acg ggt tat          4086
Arg Thr Lys Ala Met Val Ala Cys Tyr Pro Gly Asn Gly Thr Gly Tyr
295                     300                     305                     310 gta cgt cat gtt gat aat cca aat gga gat gga aga tgt gtg aca tgt          4134
Val Arg His Val Asp Asn Pro Asn Gly Asp Gly Arg Cys Val Thr Cys
                    315                     320                     325 ata tat tat ctt aat aaa gac tgg gat gcc aag gta agt gga ggt ata          4182
Ile Tyr Tyr Leu Asn Lys Asp Trp Asp Ala Lys Val Ser Gly Gly Ile
                330                     335                     340 ctt cga att ttt cca gaa ggc aaa gcc cag ttt gct gac att gaa ccc          4230
Leu Arg Ile Phe Pro Glu Gly Lys Ala Gln Phe Ala Asp Ile Glu Pro
            345                     350                     355 aaa ttt gat aga ctg ctg ttt ttc tgg tct gac cgt gcc aac cct cat          4278
Lys Phe Asp Arg Leu Leu Phe Phe Trp Ser Asp Arg Arg Asn Pro His
        360                     365                     370 gaa gta caa cca gca tat gct aca agg tac gca ata act gtt tgg tat          4326
Glu Val Gln Pro Ala Tyr Ala Thr Arg Tyr Ala Ile Thr Val Trp Tyr
375                     380                     385                     390 ttt gat gca gat gag aga gca cga gct aaa gta aaa tat cta aca ggt          4374
Phe Asp Ala Asp Glu Arg Ala Arg Ala Lys Val Lys Tyr Leu Thr Gly
                    395                     400                     405 gaa aaa ggt gtg agg gtt gaa ctc aat aaa cct tca gat tcg gtc ggt          4422
```

```
Glu Lys Gly Val Arg Val Glu Leu Asn Lys Pro Ser Asp Ser Val Gly
            410                 415                 420 aaa gac gtc ttc tagagccttt gatccagcaa taccccactt cacctacaat      4474
Lys Asp Val Phe
        425 attgttaact atttgttaac ttgtgaatac gaataaatgg gataaagaaa aatagacaac  4534 cagttcgcat tttaataagg aaacagaaac aacttttgt gttgcatcaa acagaagatt  4594 ttgactgctg tgactttgta ctgcatgatc aacttcaaat ctgtgattgc ttacaggagg  4654 aagataagct actaattgaa aatggttttt acatctggat atgaaataag tgccctgtgt  4714 agaattttt tcattcttat attttgccag atctgttatc tagctgagtt catttcatct  4774 ctccctttt tatatcaagt ttgaatttgg gataattttt ctatattagg tacaatttat  4834 ctaaactgaa ttgagaaaaa attacagtat tattcctcaa aataacatca atctatttt   4894 gtaaacctgt tcatactatt aaattttgcc ctaaaagacc tcttaataat gattgttgcc  4954 agtgactgat gattaatttt attttactta aaataagaaa aggagcactt taattacaac  5014 tgaaaaatca gattgttttg cagtccttcc ttacactaat ttgaactctt aaagattgct  5074 gcttttttt tgacattgtc aataacgaaa cctaattgta aaacagtcac catttactac  5134 caataacttt tagttaatgt tttacaagg                                    5163

<210> SEQ ID NO 4
<211> LENGTH: 426
<212> TYPE: PRT
<213> ORGANISM: Homo sapiens

<400> SEQUENCE: 4

Met Ala Asn Asp Ser Gly Gly Pro Gly Gly Pro Ser Pro Ser Glu Arg
 1               5                  10                  15

Asp Arg Gln Tyr Cys Glu Leu Cys Gly Lys Met Glu Asn Leu Leu Arg
            20                  25                  30

Cys Ser Arg Cys Arg Ser Ser Phe Tyr Cys Cys Lys Glu His Gln Arg
        35                  40                  45

Gln Asp Trp Lys Lys His Lys Leu Val Cys Gln Gly Ser Glu Gly Ala
    50                  55                  60

Leu Gly His Gly Val Gly Pro His Gln His Ser Gly Pro Ala Pro Pro
65                  70                  75                  80

Ala Ala Val Pro Pro Pro Arg Ala Gly Ala Arg Glu Pro Arg Lys Ala
                85                  90                  95

Ala Ala Arg Arg Asp Asn Ala Ser Gly Asp Ala Ala Lys Gly Lys Val
            100                 105                 110

Lys Ala Lys Pro Pro Ala Asp Pro Ala Ala Ala Ser Pro Cys Arg
        115                 120                 125

Ala Ala Ala Gly Gly Gln Gly Ser Ala Val Ala Glu Ala Glu Pro
    130                 135                 140

Gly Lys Glu Glu Pro Pro Ala Arg Ser Ser Leu Phe Gln Glu Lys Ala
145                 150                 155                 160

Asn Leu Tyr Pro Pro Ser Asn Thr Pro Gly Asp Ala Leu Ser Pro Gly
                165                 170                 175

Gly Gly Leu Arg Pro Asn Gly Gln Thr Lys Pro Leu Pro Ala Leu Lys
            180                 185                 190

Leu Ala Leu Glu Tyr Ile Val Pro Cys Met Asn Lys His Gly Ile Cys
        195                 200                 205

Val Val Asp Asp Phe Leu Gly Lys Glu Thr Gly Gln Gln Ile Gly Asp
```

```
                   210                 215                 220
Glu Val Arg Ala Leu His Asp Thr Gly Lys Phe Thr Asp Gly Gln Leu
225                 230                 235                 240

Val Ser Gln Lys Ser Asp Ser Lys Asp Ile Arg Gly Asp Lys Ile
                245                 250                 255

Thr Trp Ile Glu Gly Lys Glu Pro Gly Cys Glu Thr Ile Gly Leu Leu
                260                 265                 270

Met Ser Ser Met Asp Asp Leu Ile Arg His Cys Asn Gly Lys Leu Gly
                275                 280                 285

Ser Tyr Lys Ile Asn Gly Arg Thr Lys Ala Met Val Ala Cys Tyr Pro
                290                 295                 300

Gly Asn Gly Thr Gly Tyr Val Arg His Val Asp Asn Pro Asn Gly Asp
305                 310                 315                 320

Gly Arg Cys Val Thr Cys Ile Tyr Tyr Leu Asn Lys Asp Trp Asp Ala
                325                 330                 335

Lys Val Ser Gly Gly Ile Leu Arg Ile Phe Pro Glu Gly Lys Ala Gln
                340                 345                 350

Phe Ala Asp Ile Glu Pro Lys Phe Asp Arg Leu Leu Phe Phe Trp Ser
                355                 360                 365

Asp Arg Arg Asn Pro His Glu Val Gln Pro Ala Tyr Ala Thr Arg Tyr
                370                 375                 380

Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
                405                 410                 415

Pro Ser Asp Ser Val Gly Lys Asp Val Phe
                420                 425

<210> SEQ ID NO 5
<211> LENGTH: 2770
<212> TYPE: DNA
<213> ORGANISM: Homo sapiens
<220> FEATURE:
<221> NAME/KEY: CDS
<222> LOCATION: (327)..(1043)

<400> SEQUENCE: 5
gagtctggcc gcagtcgcgg cagtggtggc ttcccatccc caaaaggcgc cctccgactc      60
cttgcgccgc actgctcgcc gggccagtcc ggaaacgggt cgtggagctc cgcaccactc     120
ccgctggttc ccgaaggcag atcccttctc ccgagagttg cgagaaactt tcccttgtcc     180
ccgacgctgc agcggctcgg gtaccgtggc agccgcaggt ttctgaaccc cgggccacgc     240
tccccgcgcc tcggcttcgc gctcgtgtag atcgttccct ctctggttgc acgctgggga     300
tcccggacct cgattctgcg ggcgag atg ccc ctg gga cac atc atg agg ctg      353
                                Met Pro Leu Gly His Ile Met Arg Leu
                                  1               5 gac ctg gag aaa att gcc ctg gag tac atc gtg ccc tgt ctg cac gag      401
Asp Leu Glu Lys Ile Ala Leu Glu Tyr Ile Val Pro Cys Leu His Glu
 10                  15                  20                  25 gtg ggc ttc tgc tac ctg gac aac ttc ctg ggc gag gtg gtg ggc gac      449
Val Gly Phe Cys Tyr Leu Asp Asn Phe Leu Gly Glu Val Val Gly Asp
                 30                  35                  40 tgc gtc ctg gag cgc gtc aag cag ctg cac tgc acc ggg gcc ctg cgg      497
Cys Val Leu Glu Arg Val Lys Gln Leu His Cys Thr Gly Ala Leu Arg
             45                  50                  55 gac ggc cag ctg gcg ggg ccg cgc gcc ggc gtc tcc aag cga cac ctg      545
```

```
                    Asp Gly Gln Leu Ala Gly Pro Arg Ala Gly Val Ser Lys Arg His Leu
                                    60                  65                  70 cgg ggc gac cag atc acg tgg atc ggg ggc aac gag gag ggc tgc gag              593
Arg Gly Asp Gln Ile Thr Trp Ile Gly Gly Asn Glu Glu Gly Cys Glu
         75                  80                  85 gcc atc agc ttc ctc ctg tcc ctc atc gac agg ctg gtc ctc tac tgc              641
Ala Ile Ser Phe Leu Leu Ser Leu Ile Asp Arg Leu Val Leu Tyr Cys
 90                  95                 100                 105 ggg agc cgg ctg ggc aaa tac tac gtc aag gag agg tct aag gca atg              689
Gly Ser Arg Leu Gly Lys Tyr Tyr Val Lys Glu Arg Ser Lys Ala Met
                    110                 115                 120 gtg gct tgc tat ccg gga aat gga aca ggt tat gtt cgc cac gtg gac              737
Val Ala Cys Tyr Pro Gly Asn Gly Thr Gly Tyr Val Arg His Val Asp
                    125                 130                 135 aac ccc aac ggt gat ggt cgc tgc atc acc tgc atc tac tat ctg aac              785
Asn Pro Asn Gly Asp Gly Arg Cys Ile Thr Cys Ile Tyr Tyr Leu Asn
                    140                 145                 150 aag aat tgg gat gcc aag cta cat ggt ggg atc ctg cgg ata ttt cca              833
Lys Asn Trp Asp Ala Lys Leu His Gly Gly Ile Leu Arg Ile Phe Pro
             155                 160                 165 gag ggg aaa tca ttc ata gca gat gtg gag ccc att ttt gac aga ctc              881
Glu Gly Lys Ser Phe Ile Ala Asp Val Glu Pro Ile Phe Asp Arg Leu
170                 175                 180                 185 ctg ttc ttc tgg tca gat cgt agg aac cca cac gaa gtg cag ccc tct              929
Leu Phe Phe Trp Ser Asp Arg Arg Asn Pro His Glu Val Gln Pro Ser
                        190                 195                 200 tac gca acc aga tat gct atg act gtc tgg tac ttt gat gct gaa gaa              977
Tyr Ala Thr Arg Tyr Ala Met Thr Val Trp Tyr Phe Asp Ala Glu Glu
                205                 210                 215 agg gca gaa gcc aaa aag aaa ttc agg aat tta act agg aaa act gaa             1025
Arg Ala Glu Ala Lys Lys Lys Phe Arg Asn Leu Thr Arg Lys Thr Glu
            220                 225                 230 tct gcc ctc act gaa gac tgaccgtgct ctgaaatctg ctggccttgt                    1073
Ser Ala Leu Thr Glu Asp
    235 tcatttagt  aacggttcct  gaattctctt  aaattctttg  agatccaaag  atggcctctt       1133
cagtgacaac  aatctccctg  ctacttcttg  catccttcac  atccctgtct  tgtgtgtggt      1193
acttcatgtt  ttcttgccaa  gactgtgttg  atcttcagat  actctctttg  ccagatgaag      1253
ttatttgcta  actccagaaa  ttcctgcaga  catcctactc  ggccagcggt  ttacctgata      1313
gattcggtaa  tactatcaag  agaagagcct  aggagcacag  cgagggaatg  aaccttactt      1373
gcactttatg  tatacttcct  gatttgaaag  gaggaggttt  gaaaagaaaa  aaatggaggt      1433
ggtagatgcc  acagagaggc  atcacggaag  ccttaacagc  aggaaacaga  gaaatttgtg      1493
tcatctgaac  aatttccaga  tgttcttaat  ccagggctgt  tggggtttct  ggagaattat      1553
cacaacctaa  tgacattaat  acctctagaa  agggctgctg  tcatagtgaa  caatttataa      1613
gtgtcccatg  gggcagacac  tcctttttc   ccagtcctgc  aacctggatt  ttctgcctca      1673
gctccatttt  gctgaaaata  atgactttct  gaataaagat  ggcaacacaa  ttttttctcc      1733
attttcagtt  cttacctggg  aacctaattc  cccagaagct  aaaaaactag  acattagttg      1793
ttttggttgc  tttgttggaa  tggaatttaa  atttaaatga  aaggaaaaat  atatccctgg      1853
tagttttgtg  ttaaccactg  ataactgtgg  aaagagctag  gtctactgat  atacaataaa      1913
catgtgtgca  tcttgaacaa  tttgagaggg  gaggtggagt  tggaaatgtg  ggtgttcctg      1973
tttttttttt  tttttttttt  tttttttagt  tttccttttt  aatgagctca  cccttttaaca     2033
```

-continued

```
caaaaaaagc agggtgatgt attttaaaaa aggaagtgga aataaaaaaa tctcaaagct    2093
atttgagttc tcgtctgtcc ctagcagtct ttcttcagct cacttggctc tctagatcca    2153
ctgtggttgg cagtatgacc agaatcatgg aacttgctag aactgtggaa gcttctactc    2213
ctgcagtaag cacagatcgc actgcctcaa taacttggta ttgagcacgt attttgcaaa    2273
agctactttt cctagttttc agtattactt tcatgtttta aaaatcccct taatttcttg    2333
cttgaaaatc ccatgaacat aaagagcca gaaatatttt cctttgttat gtacggatat     2393
atatatatat atagtcttcc aagatagaag tttactttt cctcttctgg ttttggaaaa     2453
tttccagata agacatgtca ccattaattc tcaacgactg ctctattttg ttgtacggta    2513
atagttatca ccttctaaat tactatgtaa tttactcact tattatgttt attgtcttgt    2573
atcctttctc tggagtgtaa gcacaatgaa gacaggaatt ttgtatattt ttaaccaatg    2633
caacatactc tcagcaccta aaatagtgcc gggaacatag taagggctca gtaaatactt    2693
gttgaataaa ctcagtctcc tacattagca ttctaaaaaa aaaaaaaaaa aaaaaaaaa     2753 aaaaaaaaaa aaaaag                                                    2770
```

```
<210> SEQ ID NO 6
<211> LENGTH: 239
<212> TYPE: PRT
<213> ORGANISM: Homo sapiens

<400> SEQUENCE: 6

Met Pro Leu Gly His Ile Met Arg Leu Asp Leu Glu Lys Ile Ala Leu
  1               5                  10                  15

Glu Tyr Ile Val Pro Cys Leu His Glu Val Gly Phe Cys Tyr Leu Asp
             20                  25                  30

Asn Phe Leu Gly Glu Val Val Gly Asp Cys Val Leu Glu Arg Val Lys
         35                  40                  45

Gln Leu His Cys Thr Gly Ala Leu Arg Asp Gly Gln Leu Ala Gly Pro
     50                  55                  60

Arg Ala Gly Val Ser Lys Arg His Leu Arg Gly Asp Gln Ile Thr Trp
 65                  70                  75                  80

Ile Gly Gly Asn Glu Glu Gly Cys Glu Ala Ile Ser Phe Leu Leu Ser
                 85                  90                  95

Leu Ile Asp Arg Leu Val Leu Tyr Cys Gly Ser Arg Leu Gly Lys Tyr
            100                 105                 110

Tyr Val Lys Glu Arg Ser Lys Ala Met Val Ala Cys Tyr Pro Gly Asn
        115                 120                 125

Gly Thr Gly Tyr Val Arg His Val Asp Asn Pro Asn Gly Asp Gly Arg
    130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
            180                 185                 190

Arg Asn Pro His Glu Val Gln Pro Ser Tyr Ala Thr Arg Tyr Ala Met
        195                 200                 205

Thr Val Trp Tyr Phe Asp Ala Glu Glu Arg Ala Glu Ala Lys Lys Lys
    210                 215                 220

Phe Arg Asn Leu Thr Arg Lys Thr Glu Ser Ala Leu Thr Glu Asp
225                 230                 235
```